(12) United States Patent
Richardson

(10) Patent No.: US 9,044,371 B2
(45) Date of Patent: Jun. 2, 2015

(54) SCALABLE AND PORTABLE HUMAN REMAINS COLD STORAGE SYSTEM

(75) Inventor: Michael P. Richardson, Anderson, SC (US)

(73) Assignee: Trailerlogic, LLC, Greenville, SC (US)

( * ) Notice: Subject to any disclaimer, the term of this patent is extended or adjusted under 35 U.S.C. 154(b) by 1580 days.

(21) Appl. No.: 12/080,118

(22) Filed: Apr. 1, 2008

(65) Prior Publication Data

US 2008/0307822 A1    Dec. 18, 2008

Related U.S. Application Data

(60) Provisional application No. 60/934,325, filed on Jun. 13, 2007.

(51) Int. Cl.
| | |
|---|---|
| *F25D 17/02* | (2006.01) |
| *F25D 11/04* | (2006.01) |
| *F28F 7/00* | (2006.01) |
| *A61G 17/00* | (2006.01) |
| *A61F 7/00* | (2006.01) |
| *A61G 17/06* | (2006.01) |

(52) U.S. Cl.
CPC .............. *A61G 17/002* (2013.01); *F25D 17/02* (2013.01); *A61G 17/06* (2013.01); *A61G 2203/46* (2013.01)

(58) Field of Classification Search
CPC ....... A61G 10/02; A61G 10/005; A61G 7/00; A61G 2203/46; A61F 7/00; A61F 7/0097; A61F 7/0085; A61F 2007/0056; A61F 2007/0076
USPC ........... 62/259.3, 430, 434, 436, 438; 165/46; 27/11; 2/458; 607/104
See application file for complete search history.

(56) References Cited

U.S. PATENT DOCUMENTS

| | | | | |
|---|---|---|---|---|
| 311,764 | A | | 2/1885 | Johnson |
| 2,726,658 | A | * | 12/1955 | Chessey .......................... 62/434 |
| 2,978,225 | A | | 4/1961 | Dallas, Jr. |
| 3,211,216 | A | * | 10/1965 | Coleman, Jr. .................... 165/46 |
| 3,435,494 | A | * | 4/1969 | Bernard ............................ 27/11 |
| 3,630,039 | A | * | 12/1971 | Hayashi ....................... 62/259.3 |
| 3,648,765 | A | * | 3/1972 | Starr ............................... 165/46 |
| 3,683,902 | A | * | 8/1972 | Artemenko et al. ............. 165/46 |

(Continued)

FOREIGN PATENT DOCUMENTS

| | | |
|---|---|---|
| CA | 2689678 A1 | 4/2008 |
| FR | 2059684 | 8/1970 |

(Continued)

OTHER PUBLICATIONS

Adroit Soft-Temp sales brochure used from 1999 to 2004.

(Continued)

*Primary Examiner* — Ljiljana Ciric
(74) *Attorney, Agent, or Firm* — Nelson Mullins Riley & Scarborough LLP

(57) ABSTRACT

The present invention is a scalable and portable human remains cold storage system having a chiller unit for providing a chilled fluid to a remains chilling bag. A flow divider manifold fluidly communicates with the chiller unit for dispersing the chilled fluid to the remains chilling bag and then channeling warmed fluid back to the chiller unit for re-chilling through a series of supply lines. The fluid flows through a continuous cycle to maintain a desired temperature within the remains chilling bag.

20 Claims, 6 Drawing Sheets

(56) References Cited

U.S. PATENT DOCUMENTS

| | | | | |
|---|---|---|---|---|
| 3,738,367 | A | * | 6/1973 | Hardy .................. 165/46 |
| 3,741,849 | A | * | 6/1973 | Hardy .................. 165/46 |
| 3,743,012 | A | * | 7/1973 | Laxo .................. 165/46 |
| 3,869,871 | A | * | 3/1975 | Rybalko et al. .................. 165/46 |
| 3,945,094 | A | * | 3/1976 | Daran et al. .................. 27/11 |
| 3,995,621 | A | * | 12/1976 | Fletcher et al. .................. 600/474 |
| 4,024,730 | A | * | 5/1977 | Bell et al. .................. 62/259.3 |
| 4,132,262 | A | | 1/1979 | Wibell |
| 4,149,541 | A | | 4/1979 | Gammons et al. |
| 4,459,468 | A | * | 7/1984 | Bailey .................. 607/104 |
| 4,691,762 | A | | 9/1987 | Elkins et al. |
| 4,718,429 | A | * | 1/1988 | Smidt .................. 607/104 |
| 4,753,268 | A | * | 6/1988 | Palau .................. 137/595 |
| 4,773,230 | A | * | 9/1988 | Garrett .................. 27/11 |
| 4,844,072 | A | * | 7/1989 | French et al. .................. 607/104 |
| 4,846,176 | A | * | 7/1989 | Golden .................. 607/104 |
| 4,951,665 | A | * | 8/1990 | Schneider .................. 607/104 |
| 4,962,761 | A | * | 10/1990 | Golden .................. 607/104 |
| 4,971,056 | A | * | 11/1990 | Seacord .................. 607/104 |
| 4,982,736 | A | * | 1/1991 | Schneider .................. 607/104 |
| 4,998,415 | A | * | 3/1991 | Larsen .................. 62/259.3 |
| 5,051,562 | A | * | 9/1991 | Bailey et al. .................. 219/506 |
| 5,054,290 | A | | 10/1991 | Hogan |
| 5,183,039 | A | * | 2/1993 | Sarian et al. .................. 165/46 |
| 5,241,951 | A | | 9/1993 | Mason et al. |
| 5,269,369 | A | * | 12/1993 | Faghri .................. 607/104 |
| 5,330,519 | A | * | 7/1994 | Mason et al. .................. 607/104 |
| 5,344,436 | A | * | 9/1994 | Fontenot et al. .................. 607/104 |
| 5,386,823 | A | * | 2/1995 | Chen .................. 165/46 |
| 5,411,541 | A | * | 5/1995 | Bell et al. .................. 607/104 |
| 5,613,730 | A | | 3/1997 | Bluie et al. |
| 5,659,933 | A | | 8/1997 | McWilliams |
| 5,711,155 | A | * | 1/1998 | DeVilbiss et al. .................. 62/434 |
| 5,755,275 | A | * | 5/1998 | Rose et al. .................. 165/46 |
| 5,806,335 | A | | 9/1998 | Herbert et al. |
| 5,894,615 | A | * | 4/1999 | Alexander .................. 165/46 |
| 5,924,181 | A | | 7/1999 | Takasugi |
| 6,109,338 | A | * | 8/2000 | Butzer .................. 165/46 |
| 6,230,501 | B1 | * | 5/2001 | Bailey et al. .................. 62/51.1 |
| 6,238,427 | B1 | * | 5/2001 | Matta .................. 607/104 |
| 6,295,819 | B1 | * | 10/2001 | Mathiprakasam et al. ...... 62/3.3 |
| 6,565,699 | B1 | * | 5/2003 | Szczesuil et al. .................. 2/458 |
| 6,584,798 | B2 | * | 7/2003 | Schegerin .................. 62/259.3 |
| D492,773 | S | * | 7/2004 | Ellingboe et al. .................. D24/129 |
| 6,827,728 | B2 | * | 12/2004 | Ellingboe et al. .................. 607/104 |
| 6,915,641 | B2 | * | 7/2005 | Harvie .................. 62/259.3 |
| 6,942,015 | B1 | * | 9/2005 | Jenkins .................. 165/46 |
| 7,373,969 | B2 | * | 5/2008 | Chambers .................. 165/46 |
| 7,377,935 | B2 | * | 5/2008 | Schock et al. .................. 607/104 |
| 7,658,205 | B1 | * | 2/2010 | Edelman et al. .................. 137/594 |
| 7,666,213 | B2 | * | 2/2010 | Freedman et al. .................. 607/104 |
| 7,823,625 | B2 | * | 11/2010 | Gammons .................. 165/46 |
| 8,216,290 | B2 | * | 7/2012 | Shawver et al. .................. 607/104 |
| 8,292,594 | B2 | * | 10/2012 | Tracey et al. .................. 417/43 |
| 8,357,188 | B2 | * | 1/2013 | Boynton et al. .................. 607/104 |
| 8,372,129 | B2 | * | 2/2013 | Baumann .................. 607/104 |
| 8,425,582 | B2 | * | 4/2013 | Schock et al. .................. 607/104 |
| 8,435,277 | B2 | * | 5/2013 | Schock et al. .................. 607/104 |
| 8,435,278 | B2 | * | 5/2013 | Callister et al. .................. 607/104 |
| 8,475,508 | B2 | * | 7/2013 | Munson .................. 607/104 |
| 8,491,645 | B2 | * | 7/2013 | Anderson et al. .................. 607/104 |
| 2002/0153126 | A1 | * | 10/2002 | Clemente .................. 165/46 |
| 2003/0029182 | A1 | * | 2/2003 | Augustine et al. .................. 165/46 |
| 2003/0098143 | A1 | * | 5/2003 | Winkle .................. 165/46 |
| 2003/0131967 | A1 | * | 7/2003 | Weder .................. 165/46 |
| 2004/0079517 | A1 | * | 4/2004 | Bueley et al. .................. 165/46 |
| 2004/0252918 | A1 | | 12/2004 | Yu et al. |
| 2006/0048520 | A1 | | 3/2006 | Huang et al. |
| 2007/0085340 | A1 | | 4/2007 | Gammons |
| 2007/0118194 | A1 | | 5/2007 | Mason et al. |
| 2008/0063771 | A1 | | 3/2008 | Dumm |
| 2009/0199571 | A1 | * | 8/2009 | Creech et al. .................. 165/46 |
| 2009/0240312 | A1 | | 9/2009 | Koewler |
| 2009/0264969 | A1 | | 10/2009 | Gammons |
| 2010/0186435 | A1 | | 7/2010 | Vogel et al. |
| 2011/0073274 | A1 | * | 3/2011 | Brummitt et al. .................. 165/46 |
| 2013/0090709 | A1 | * | 4/2013 | Machold et al. .................. 607/104 |

FOREIGN PATENT DOCUMENTS

| | | |
|---|---|---|
| FR | 2539620 A | 7/1984 |
| GB | 2457627 A | 8/2009 |
| JP | 409253141 A | 9/1997 |
| JP | 409286701 A | 11/1997 |
| JP | 2006167418 | 6/2006 |
| JP | 2006346428 | 12/2006 |
| WO | WO 97/24088 A1 | 7/1997 |
| WO | WO 98/23236 A1 | 6/1998 |
| WO | WO 2008/135710 A2 | 11/2008 |

OTHER PUBLICATIONS

Bernard et al., Treatment of Comatose Survivors of Out-of-Hospital Cardiac Arrest with Induced Hypothermia, Retrieved from the Internet: <URL:http://hypothermia.emcrit.org/hypoarts/bernard.pdf> (retrieved on Jan. 27, 2011).

PCT Invitation to Pay Additional Fees and, where applicable, protest fee, dated Dec. 17, 2010, for International Application No. PCT/US2010/048383.

PCT Notification of Transmittal of the International Search Report and the written opinion of the International Searching Authority, or the declaration, PCT International Search Report, PCT Written Opinion of the International Searching Authority, dated Feb. 17, 2011, for International Application No. PCT/US2010/060991.

PCT International Preliminary Report on Patentability and Written Opinion of the International Searching Authority for PCT Patent Application No. PCT/US2010/048383.

* cited by examiner

US 9,044,371 B2

SCALABLE AND PORTABLE HUMAN REMAINS COLD STORAGE SYSTEM

CROSS REFERENCE TO RELATED APPLICATION

This application claims priority from U.S. Provisional Application Ser. No. 60/934,325, filed Jun. 13, 2007.

BACKGROUND OF THE INVENTION

1) Field of the Invention

The present invention relates to a cold storage remains system, and more particularly, to a portable remains cooling system having a series of storage pouches with a cold fluid tubing network connected to a manifold system and a chiller for cycling cold fluid through the tubing network to maintain a desired temperature in the storage pouches.

2) Description of Related Art

In dealing with mass casualty situations, maintaining remains in a refrigerated condition for an extended period of time presents substantial logistical concerns. For example, in the U.S. Military, the standards for dealing with human remains require 40 to 60 pounds of ice per remains to maintain the remains at a chilled temperature for approximately 10 hours. In a war time setting when casualties are high, this creates a serious issue of providing sufficient ice to properly handle the remains in the field and through transport to a processing facility, such as a mortuary.

In some field situation, refrigerated tractor trailers have been used to temporarily house remains. The portability of this arrangement is extremely limited due to practical matters of moving such a large trailer around and providing sufficient power to refrigerate the entire trailer to a sufficiently low near freezing temperature. Additionally, such large refrigerated systems take time to set up and are completely impractical in battlefield situations where locations are constantly changing and immediate temporary storage and cooling of the remains is required, for example, when remains are being transported from the front lines to a casualty collection point. Further, in situations where biological or chemical contamination is present, it is desired to control the remains in individual sealed containers to prevent cross-contamination with other remains, as well as to prevent infection or exposure for those dealing with the remains.

The prior art is replete with various human remains cooling systems. For example, U.S. Pat. No. 5,054,290 (Hogan) discloses a portable container able to provide refrigeration for a human corpse. The container includes an outer shell, a lining and a conduit system of tubes and hoses. A freezable liquid is released from reservoirs and flows through the connecting hoses into the flow tubes. The freezable liquid is absorbed into the container lining and frozen. The liquid is not re-circulated through the flow tubes and a chiller system to maintain a constant temperature.

U.S. Pat. No. 5,924,181 (Takasugi) shows a method of keeping a cadaver at a low temperature in a casket that includes supplying a liquefied cooling gas to the cooling chamber, which is transformed into a precipitate within the casket interior. The liquid is not re-circulated through flow tubes and a chiller system to maintain a constant temperature.

U.S. Pat. No. 0,311,764 (Johnson) shows a single corpse cooler and preserver that circulates cool gas through pipes in a casket and then vents the spent gas. There is no recirculation of the gas.

U.S. Publication No. 2004/0252918 A1 (Yu et al.) shows a body bag that includes an outer bag case and an inner bag case. Air is extracted from the bag by vacuum means. No re-circulating cooling system is disclosed to maintain the temperature inside the body bag.

Japanese Publication No. 2006346428 (Omori) shows a low-temperature cold reserving body storage bag that includes a pipeline for circulating a cooling fluid. There is no disclosure of a manifold system for circulating fluid to multiple storage bags, or that the system is adaptable to meeting the needs of a mass casualty situation.

Japanese Publication No. 409286701 A (Aoyanagi) shows injecting a liquefied gas into a bag for rapidly cooling a corpse.

Japanese Publication No. 409253141 A (Aoyanagi) shows a dead body housing storing bag that includes means for introducing a cold air into the bag and a return pipe. There is no disclosure of a manifold system for circulating fluid to multiple storage bags, or that the system is adaptable to meeting the needs of a mass casualty situation.

French Application No. 2 539 620 (Perroud et al.) shows an envelope for covering a body. The inside surface of the envelope is cooled by a network of flexible tubes through which a refrigerating medium flows. There is no disclosure of a manifold system for circulating fluid to multiple storage bags, or that the system is adaptable to meeting the needs of a mass casualty situation.

While the idea of providing cold storage for human remains is clearly known, the prior art simply has not adequately addressed the problems associated with quickly preserving mass casualties in a field environment, such as on a battlefield. The prior art does not address the concerns of portability and scalability needed in dealing with cold storage of human remains systems for mass casualty situations where biological or chemical contamination may be present. The prior art does not adequately address the logistical concerns of providing acceptable levels of rapid cooling and storage for remains in the field, and for the transport of those remains while maintaining a required level of cooling. Thus, there is a need to address the logistical concerns for a portable remains cooling system able to support numerous casualties in individual containers.

Accordingly, it is an object of the present invention to provide a cold storage remains system which utilizes a series of individual storage pouches having a cold fluid tubing network connected to a manifold system with a chiller for cycling cold fluid through the tubing network to maintain a desired temperature in the storage pouches.

It is a further object of the present invention to provide a portable cold storage remains system for dealing with mass casualties in the field.

It is a further object of the present invention to provide a scalable cold storage remains system that can be adapted to accommodate changing numbers of remains for individual storage in a field environment.

SUMMARY OF THE INVENTION

The above objectives are accomplished according to the present invention by providing a scalable and portable human remains cooling system comprising a chiller unit having a chilled fluid supply, at least one primary fluid supply line and at least one primary fluid return line for providing a chilled fluid for cooling human remains and circulating warmed fluid back to the chiller for re-chilling; a flow divider manifold including a chilled fluid input having a series of chilled fluid output ports in fluid communication with the primary fluid supply line from the chiller for receiving and dispersing the chilled fluid supply, the manifold having a warm fluid output including a series of warm fluid input ports in fluid communication with the primary fluid return line to the chiller unit for returning warmed fluid to the chiller for re-chilling; at least one secondary supply line in fluid communication with one of the chilled fluid output ports; at least one secondary return line in fluid communication with one of the warm fluid input ports; at least one remains chilling bag in fluid communication with the secondary supply line receiving the chilled fluid from the chiller unit, and in fluid communication with the secondary return line for returning warmed fluid to the chiller unit; whereby the chilled fluid is circulated through the chilling bag and warmed fluid that has circulated through the chilling bag is returned to the chiller unit for re-chilling in a continuous cycle to maintain a desired temperature within the remains chilling bag.

In a further embodiment, the storage system includes a plurality of flow divider manifolds arranged along the primary fluid supply line, wherein the chilled fluid input on each manifold is releasably connected in fluid communication with the primary fluid supply line, and the warm fluid output on each the manifold is releasably connected in fluid communication with the primary fluid return line so that the flow divider manifolds can be added and removed from the primary fluid supply line to scale the size of the system for the number of the remains chilling bags that may be required.

In a further embodiment, one of the chilled fluid output ports on a first flow divider manifold is connected in fluid communication with the chilled fluid input on a second flow divider manifold in a consecutive arrangement so that the chilled fluid from the primary fluid supply line passes through the first flow divider manifold before being received in the second flow divider manifold.

In a further embodiment, the chilled fluid is cooled to a temperature of approximately between 30° F. to 45° F. prior to circulation through the remains chilling bag. Preferably, the chilled fluid includes approximately 30% by volume of glycol to prevent freezing.

In a further embodiment, the chiller unit includes an outlet pressure reducing valve in fluid communication with the primary fluid supply line for providing a low flow pressure of the chilled fluid through the system. Preferably, the low flow pressure of the chilled fluid through the primary fluid supply line is approximately 10 psi.

In a further embodiment, the primary fluid supply line and the primary fluid return line are a 1" diameter for maintaining flow volume and pressure to the flow divider manifold. Further, the secondary supply and return lines are a ⅜" diameter for maintaining pressure and flow volume to circulate the fluid through the remains chilling bag.

In a further embodiment, the primary and secondary fluid supply lines and the primary and secondary fluid return lines are connected to the manifold using a quick connect coupling so that the supply and return lines may be connected and disconnected without turning off the chiller unit.

In a further embodiment, the remains chilling bag includes quick connect couplings for connecting in fluid communication with the secondary supply line and the secondary return line so that the remains chilling bags may be connected and disconnected without turning off the chiller unit.

In a further embodiment, the remains chilling bag includes a top outer protective layer and a bottom outer protective layer releasably interconnected forming an interior cavity for storing remains. A first cooling pad is carried by the top outer protective layer and a second cooling pad carried by the bottom outer protective layer wherein the first and second cooling pads are each connected in fluid communication with the secondary supply line and the secondary return line for circulating the chilled fluid through the bag so that the remains placed in the interior cavity are cooled simultaneously from both a top and bottom side and returning warmed fluid to the chiller.

In a further embodiment, the first and second cooling pads each include a flow director segmenting an interior fluid cavity in the cooling pads generally into a feed section and a return section so that the chilled fluid is circulated through the feed section into the return section in a consecutive one-way flow arrangement.

In a further embodiment, the interior fluid cavity of the first and second cooling pads includes a plurality of fluid dispersion cells for directing the chilled fluid throughout the feed section and the return section.

In a further embodiment, the first and second cooling pads are releasably carried by the top and bottom outer protective layers respectively for removal from the remains chilling bag.

In a further embodiment, a first charcoal filter layer is disposed between the top outer protective layer and the first cooling pad, and a second charcoal filter layer disposed between the bottom outer protective layer and the second cooling pad for absorbing odors emitted from remains placed in the interior cavity.

BRIEF DESCRIPTION OF THE DRAWINGS

The construction designed to carry out the invention will hereinafter be described; together with other features thereof. The invention will be more readily understood from a reading of the following specification and by reference to the accompanying drawings forming a part thereof, wherein an example of the invention is shown and wherein.

DETAILED DESCRIPTION OF A PREFERRED EMBODIMENT

Figure 1:
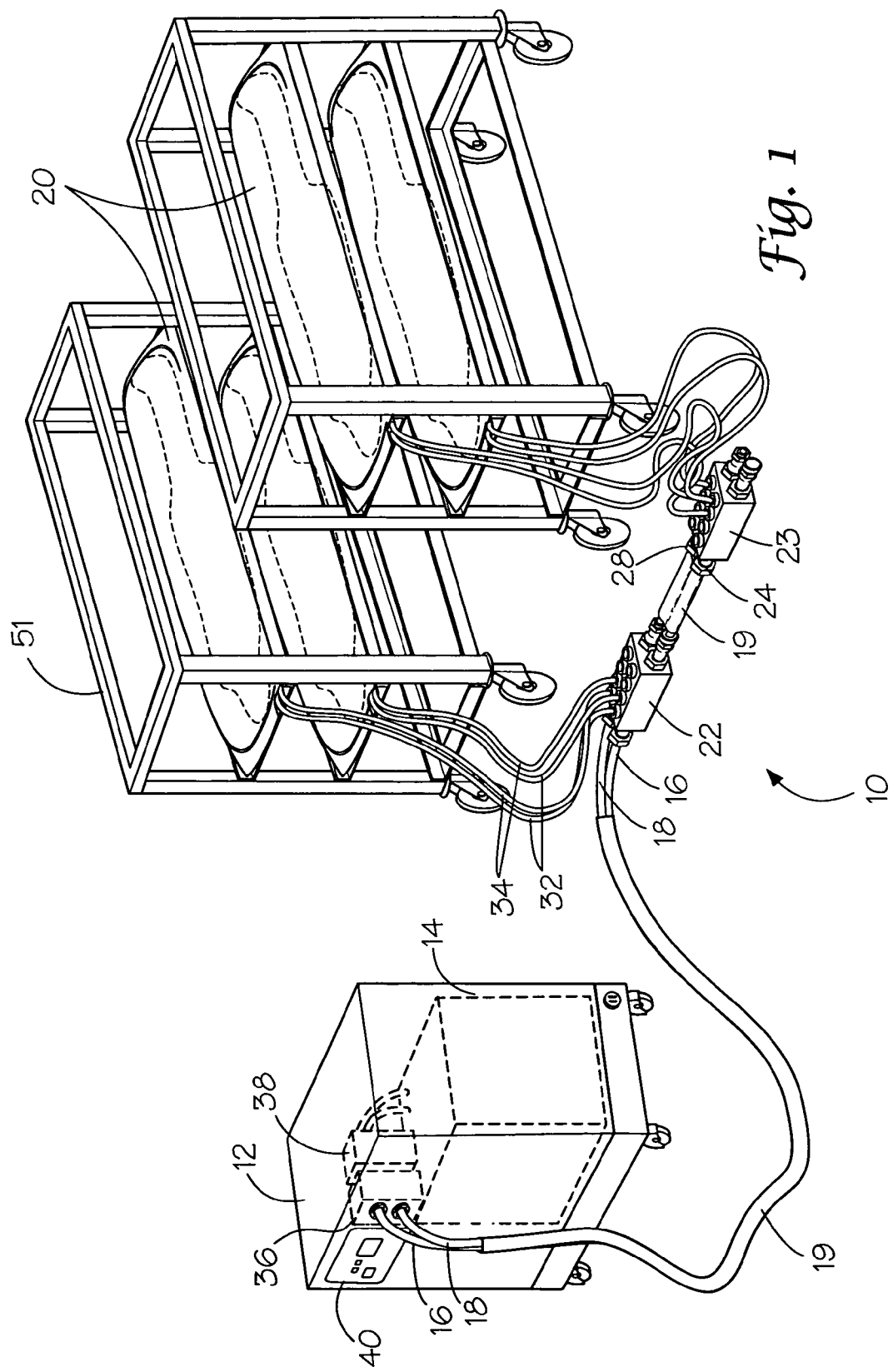
FIG. 1 shows a perspective view of a scalable and portable human remains cold storage system according to the present invention.

With reference to the drawings, the invention will now be described in more detail. Referring to FIG. 1, a scalable and portable human remains cooling system is shown, designated generally as 10. The system circulates a chill fluid through a series of remains chilling bags 20 to maintain a required core temperature of a human remain at preferably about 34°-42° F. for an indefinite period after death occurs. In each remains chilling bag 20, a pair of cooling pads is provided to be placed in direct contact with a top side and a bottom side of the human remain to achieve the desired cooling.

In the embodiment illustrated in FIG. 1, cooling system 10 includes a chiller unit 12 having a fluid container 14 holding a chilled fluid supply for circulating fluid through remains chilling bags 20. At least one primary fluid supply line 16 and at least one primary fluid return line 18 extended from chiller unit 12 for channeling the chilled fluid for cooling human remains and circulating warmed fluid back to chiller unit 12 for re-chilling.

Figure 2:
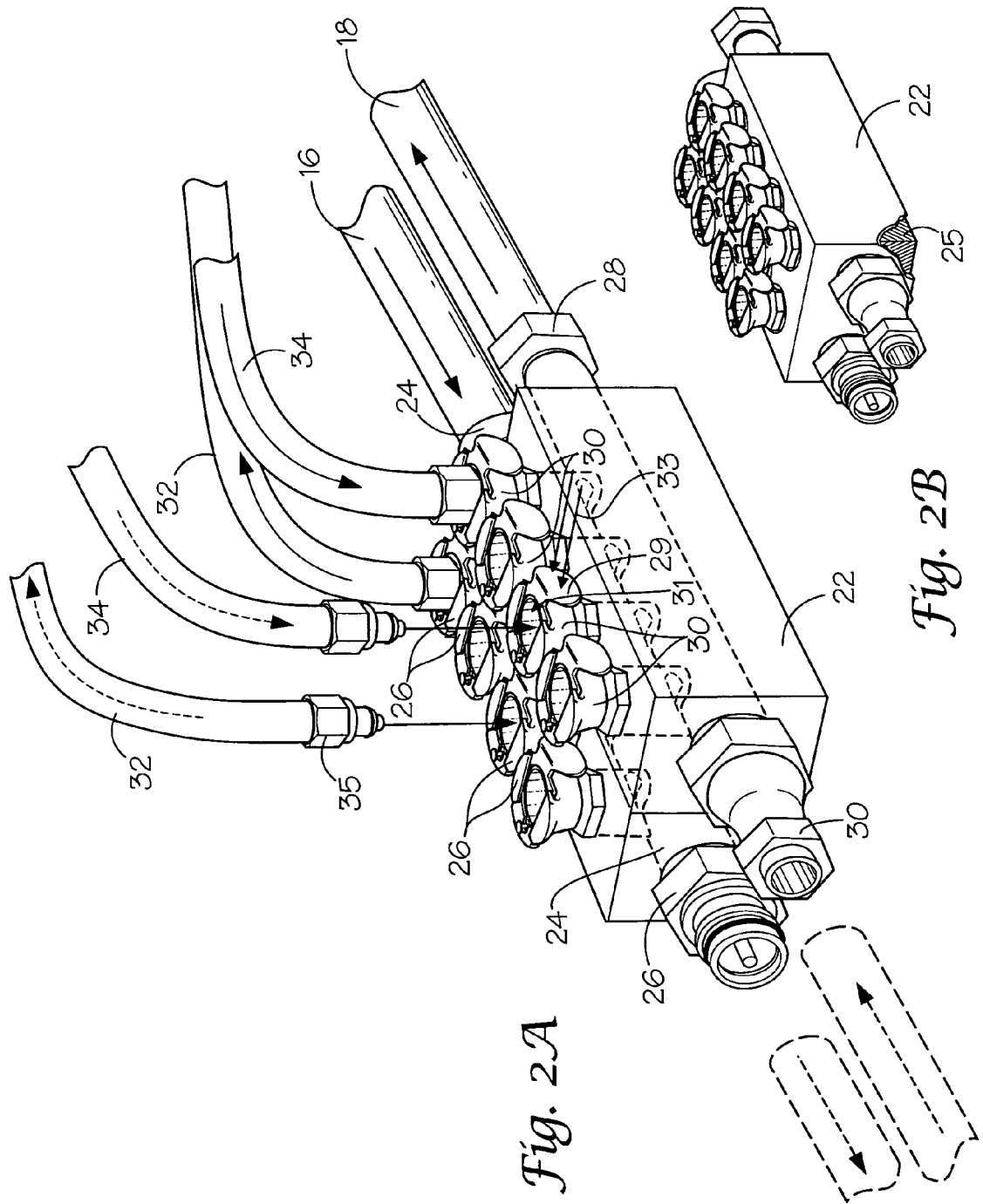
FIGS. 2A and 2B show perspective views of a flow divider manifold according to the present invention.

Referring to FIGS. 1 and 2, to disperse and direct the flow of fluid to a series of remains chilling bags 20, at least one flow divider manifold 22 is provided for channeling the chilled fluid through a plurality of remains chilling bags 20. Flow divider manifold 22 includes a chilled fluid input 24 connecting manifold 22 in fluid communication with primary fluid supply line 16. Chilled fluid input 24 carries a series of chilled fluid output ports 26 in fluid communication with primary fluid supply line 16 for channeling the chilled fluid out to remains chilling bags 20. Further, manifold 22 has a warm fluid output 28 carrying a series of warm fluid input ports 30 in fluid communication with the primary fluid return line 18 for returning warmed fluid to chiller unit 12 for re-chilling. At least one secondary supply line 32 connects in fluid communication with one of chilled fluid output ports 26 for channeling the chilled fluid into remains chilling bags 20. At least one secondary return line 34 connects in fluid communication with one of warm fluid input ports 30 for returning warmed fluid from the remains chilling bags 20 for re-chilling.

At least one remains chilling bag 20 is provided in fluid communication with secondary supply line 32 receiving the chilled fluid from chiller unit 12. The remains chilling bag 20 is also connected in fluid communication with the secondary return line 34 for returning warmed fluid to the chiller unit. Accordingly, a system is provided wherein the chilled fluid is circulated through remains chilling bag 20 and warmed fluid that has circulated through remains chilling bag 20 is returned to chiller unit 12 for re-chilling in a continuous cycle to maintain a desired temperature within remains chilling bag 20.

The chiller unit 12 cooperates with remains chilling bags 20 to circulate a chilled fluid through the bags to absorb any heat from the remains and maintain a desired internal temperature in the bag. In the preferred embodiment, chiller unit 12 includes a refrigeration circuit for cooling the fluid to a desired temperature of generally between 30°-45° F. Preferably, the temperature within remains chilling bags 20 is maintained at approximately 34°-42° F. for most temporary storage needs. A chiller unit of the type manufactured by Advantage Engineering, Inc. 525 East Stop 18 Road, Greenwood, Ind. 46142, can serve to provide and circulate a chilled fluid supply through a plurality of remains chilling bags. Preferably, the chilled fluid is a glycol and water solution or other similar fluid to maintain circulation of the fluid through the various supply lines and manifolds. In a preferred embodiment, the chilled fluid includes approximately 30% by volume of glycol to prevent freezing.

In a further embodiment, chiller unit 12 is adapted to include an outlet pressure reducing valve 36 in fluid communication with primary fluid supply line 16 for creating a low flow pressure of the chilled fluid through the system. Preferably, the low flow pressure of the chilled fluid through primary fluid supply line 16 is approximately 10 psi. In a further embodiment, primary fluid supply line 16 and primary fluid return line 18 have a one-inch diameter for maintaining flow volume and pressure to flow divider manifold 22 under the low flow pressure condition of the system. Further, secondary supply and return lines 32 and 34 have a ⅜-inch diameter for maintaining pressure and flow volume to circulate the fluid through the remains chilling bag.

The chiller unit is designed to allow for connection and disconnection of remains chilling bags 20 without having to shutdown the system by using plug connections on manifold 22 and remains chilling bags 20 that seal when the plug is removed to prevent fluid from spilling out of the manifold or the bag. Preferably, primary and secondary fluid supply lines 16 and 32 and the primary and secondary fluid return lines 18 and 34 are connected to flow divider manifold 22 using a quick connect coupling so that the supply and return lines may be connected and disconnected without turning off the chiller unit or having to use tools to complete the connections. Further, remains chilling bag 20 also includes quick connect couplings for connecting in fluid communication with secondary supply line 32 and secondary return line 34 so that remains chilling bags 20 may be connected and disconnected without turning off the chiller unit or having to use tools to complete the connections. The low flow pressure of the system allows for quick connect fittings to be used in connecting the supply lines and return lines to the manifold and the remains chilling bags.

Referring to FIG. 2A, quick connect couplings are shown on flow divider manifold 22 for connecting with secondary supply line 32 and secondary return line 34. In the illustrated embodiment, the quick connect couplings are provided on chilled fluid output ports 26 and warm fluid input ports 30. Preferably, to prevent accidental disconnect, a quick connect coupling, designated generally as 31, includes a slide latch 29 which moves laterally across the open top of the port when pressed in direction 33. When actuated in direction 33, a complementary connector 35 may be received into one of ports 26 and 30. When slide latch 29 is released, complementary connector 35 is locked into the port in fluid communication with chilled fluid input 24 or warm fluid output 28. When complementary connector 35 is removed from the port, a check valve in the port is closed to prevent fluid from leaking out of the system. It is understood that various types of quick connect couplings exist and are well known to those skilled in the art. The illustrated embodiment is provided by way of example only and other quick connect type fittings may be used to accomplish the same result, which are considered to be within the scope and spirit of the present invention. Accordingly, the present invention is not limited to only using the illustrated embodiment.

Referring to FIG. 1, primary fluid supply line 16 and primary fluid return line 18 may be covered in an insulation wrap 19 to resist warming of the chilled fluid passing through the lines. As shown in FIG. 2B, flow divider manifold may also be covered by an insulation wrap 25 to further resist warming of the chilled fluid passing through the manifold.

Referring to FIG. 1, a fluid pump 38 is included in chiller unit 12 which pressurizes the system and forces the fluid through the supply lines and into remains chilling bags 20, and circulates that fluid back to chiller unit 12 for re-chilling. Preferably, pump 38 includes a stepping motor for adapting to changes in fluid level as remains chilling bags 20 are added or removed from manifold 22. The fluid level will need to be replenished in chiller unit 12 if numerous bags are removed from the system and new bags are added. Preferably, the system is design to hold sufficient fluid to support 28 remains chilling bags with a 25 gallon fluid container 14 in chiller unit 12. Chiller unit 12 is preferably connected to ground based power, but due to the limited power demands of the system, may be run on portable power generator units or batteries in remote locations. Preferably, chiller unit 12 includes a temperature sensor and pressure display 40 operatively associated with the chilled fluid for monitoring the temperature of the fluid as it leaves the chiller unit for circulation through the remains chilling bags 20, as well as the pressure of the fluid in the lines.

As shown in FIG. 1, a plurality of flow divider manifolds 22 may be arranged along primary fluid supply line 16, wherein chilled fluid input 24 on each manifold 22 is releasably connected in fluid communication with primary fluid supply line 16, and the warm fluid output 28 on each manifold 22 is releasably connected in fluid communication with primary fluid return line 18 so that flow divider manifolds 22 can be added and removed from primary fluid supply line 16 to scale the size of the system for the number of the remains chilling bags 20 that may be required. Preferably, the releasable connections are common quick connect couplings generally as described above. In a preferred embodiment as illustrated, one of chilled fluid output ports 26 on a first flow divider manifold 22 is connected in fluid communication with chilled fluid input 24 on a second flow divider manifold 23 in a consecutive arrangement so that the chilled fluid from primary fluid supply line 16 passes through the first flow divider manifold 22 before being received in the second flow divider manifold 23. The same arrangement is provided for warm fluid return through the manifolds along primary fluid return line 18.

Figure 3:
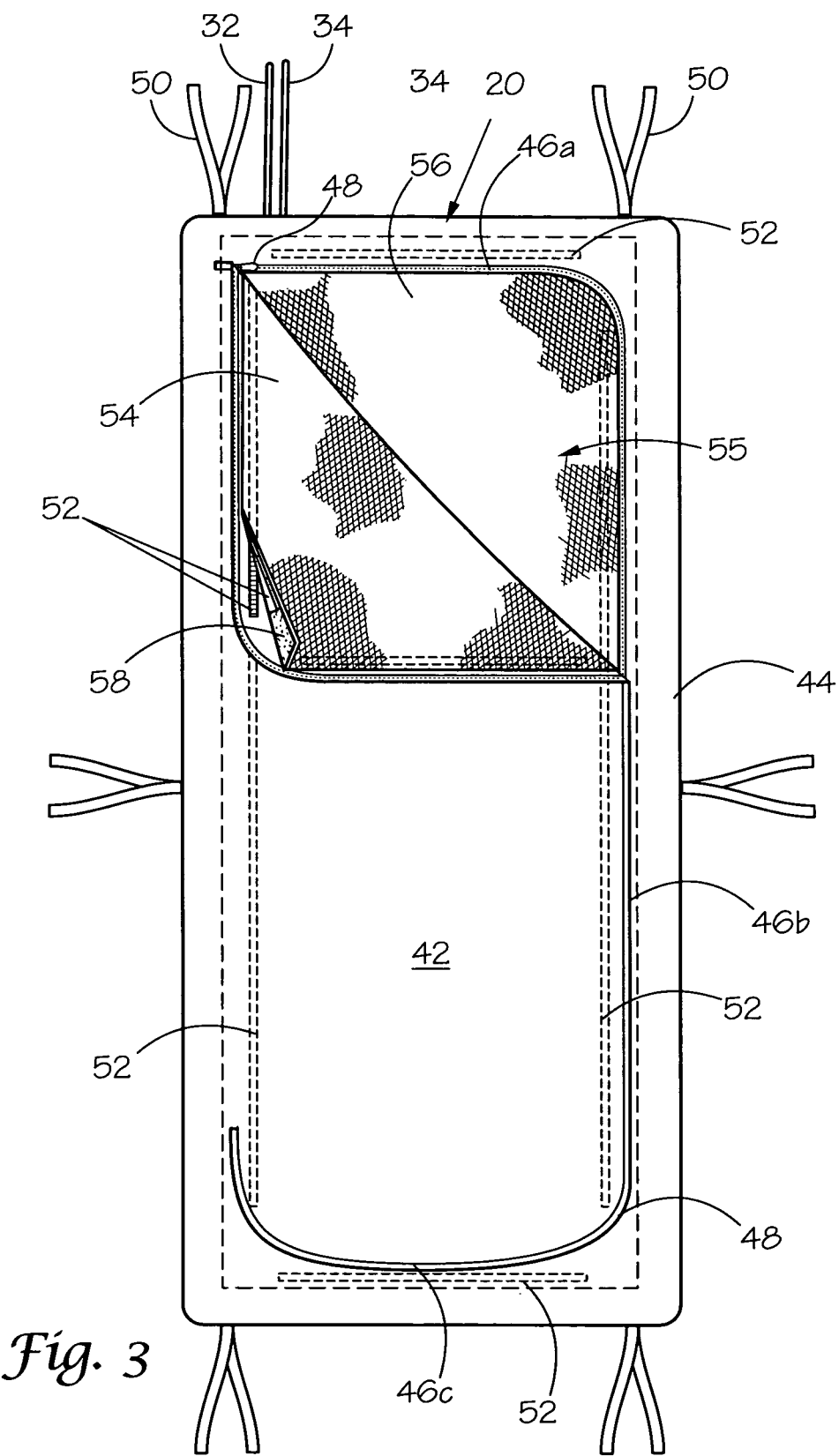
FIG. 3 shows a top plan view of a remains chilling bag according to the present invention.
Figure 4:
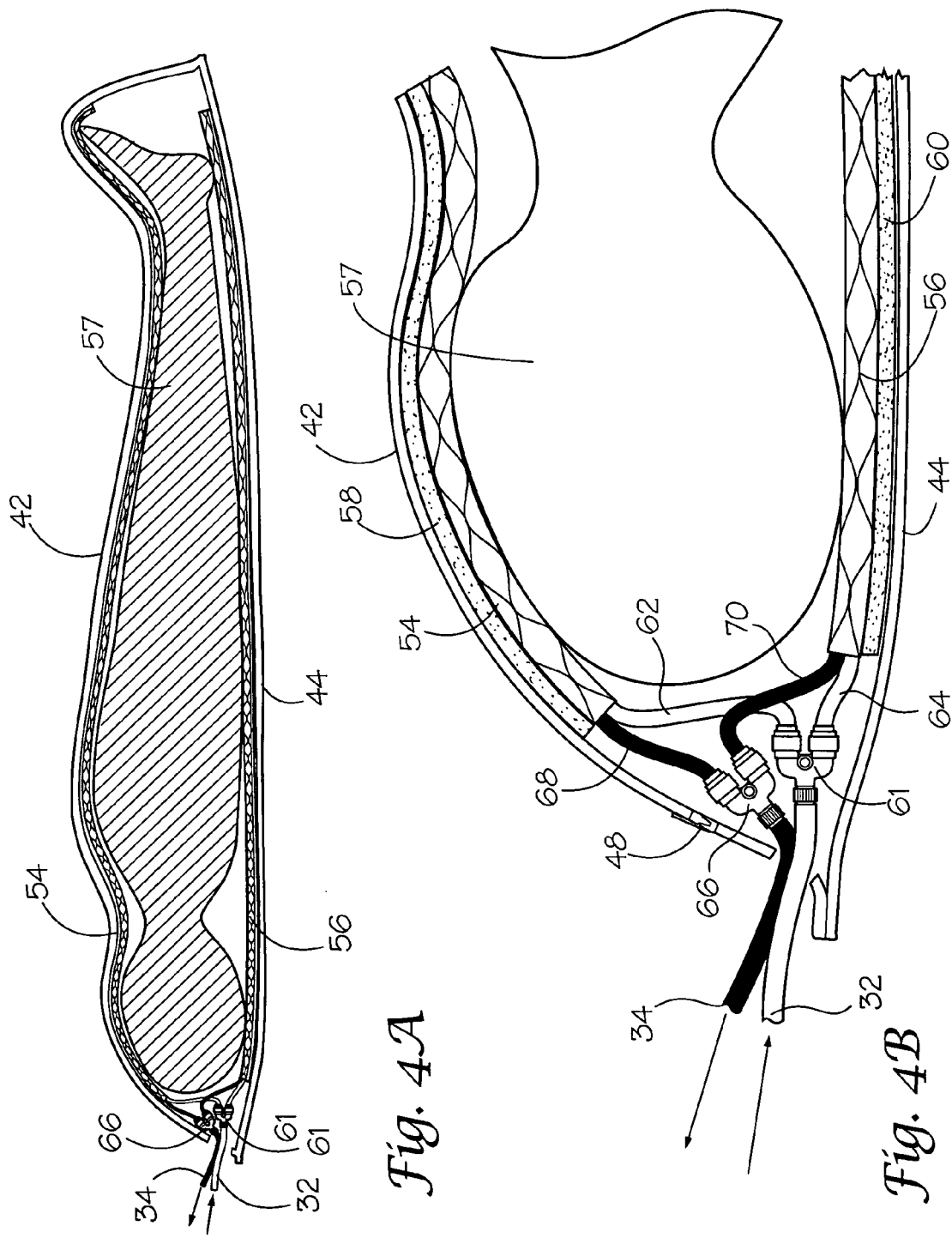
FIGS. 4A and 4B show cross-section views of a remains chilling bag according to the present invention.

Referring to FIGS. 3 and 4A, in a preferred embodiment, remains chilling bag 20 includes a top outer protective layer 42 and a bottom outer protective layer 44 releasably interconnected forming an interior cavity, designated generally as 55 for storing remains 57. Preferably, top and bottom layers 42 and 44 are releasably interconnected generally along three sides 46a-46c by a gas tight zipper 48. When unzipped, top outer protective layer 42 opens as a flap to expose interior cavity 55. Straps 50 may also be provided for securing remains chilling bags 20 to racks 51.

Referring to FIGS. 3, 4A and 4B, a first cooling pad 54 is carried by top outer protective layer 42 and a second cooling pad 56 is carried by bottom outer protective layer 44. First and second cooling pads 54 and 56 are each connected in fluid communication with secondary supply line 32 and secondary return line 34 for circulating the chilled fluid through the bag so that the remains placed in interior cavity 55 are cooled simultaneously from both a top and bottom side through direct contact of the cooling pads with remains 57. In a preferred embodiment, secondary supply line 32 is received into remains chilling bag 20 and connected to a Y-divider 61 inside remains chilling bag 20. Y-divider 61 separates the chilled fluid input into two feed lines so that a first feed line 62 extending from Y-divider 61 is connected in fluid communication with first cooling pad 54 and a second feed line 64 extending from Y-divider 61 is connected in fluid communication with second cooling pad 56. Warmed fluid that has cycled through cooling pads 54 and 56 is directed back to chiller unit 12 through return feed lines 68 and 70, which converge into a second Y-divider 66 that feeds both of return feed lines 68 and 70 into secondary return line 34 for circulating back to chiller unit 12. Preferably, Y-dividers 61 and 66 are identical and use common releasable push-together quick connect type couplings to prevent accidental disconnecting of the lines.

Referring to FIG. 4B, in a further embodiment, a first charcoal filter layer 58 is disposed between top outer protective layer 42 and first cooling pad 54. A second charcoal filter layer 60 is disposed between bottom outer protective layer 44 and second cooling pad 56. The charcoal layers help to absorb odors emitted from remains 57 placed in interior cavity 55.

Figure 5:
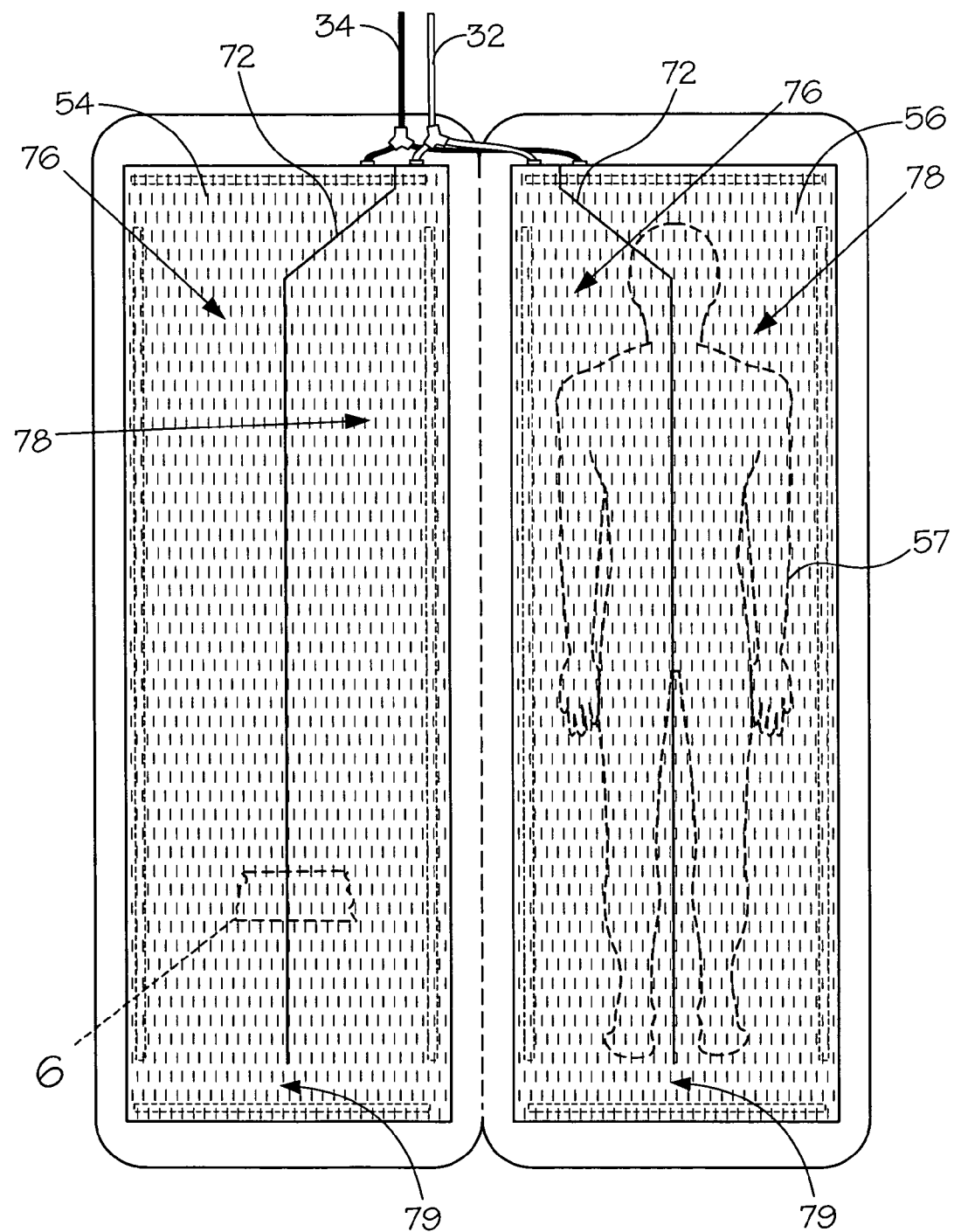
FIG. 5 shows a top view of the remains chilling bag in an open position.
Figure 6:
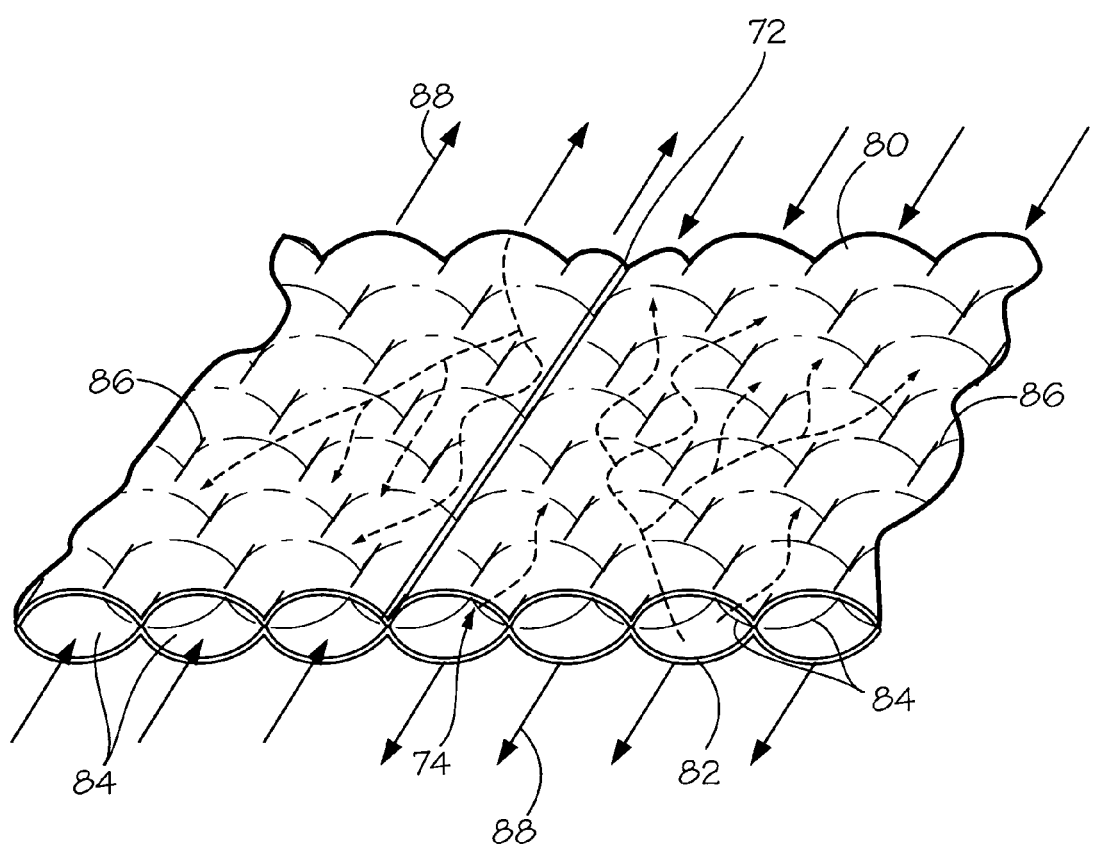
FIG. 6 shows a cut-away view of a section of the remains chilling bag from FIG. 5 according to the present invention.

Referring to FIGS. 5 and 6, in a further embodiment, the first and second cooling pads 54 and 56 each include a flow director 72 segmenting an interior fluid cavity 74 in the cooling pads generally into a feed section, designated generally as 76, and a return section 78 so that chilled fluid is circulated first through feed section 76 and then into return section 78 in a consecutive one-way flow arrangement. An opening generally at distal end 79 of each of cooling pads 54 and 56 is provided in flow director 72 so that fluid can pass from feed section 76 into return section 78. As shown in FIG. 6, flow director 72 may be formed by heat welding a top side 80 of the cooling pads to a bottom side 82 so that fluid cannot pass through flow director 72.

In a further embodiment, interior fluid cavity 74 of first and second cooling pads 54 and 56 includes a plurality of fluid dispersion cells 84 for directing the chilled fluid throughout feed section 76 and return section 78. Preferably, fluid dispersion cell 84 are formed by heat welding, as indicated by reference number 86, in a staggered arrangement sections of top side 80 and bottom side 82 of the cooling pads. Arrows 88 indicate the direction of fluid flow through the cooling pad on opposite sides of flow director 72.

Referring to FIG. 3, in a further embodiment, the first and second cooling pads 54 and 56 are releasably carried by top and bottom outer protective layers 42 and 44 for removal from remains chilling bag 20. Preferably, cooperating strips of hook and loop connectors 52 are provided generally around the perimeter of the cooling pads for interconnecting cooling pads 54 and 56 to protective layers 42 and 44 respectively. This also helps secure charcoal layers 58 and 60 in place between the cooling pads and outer protective layers 42 and 44.

Preferably, outer protective layers 42 and 44 of remains chilling bag 20 are a bio/chemical hazard approved material. In combination with cooling pads 54 and 56, and chiller unit 12, these components allow for complete long term remains chilling that meets all international, federal, and US Military requirements for the transfer of human remains both CONUS and OCONUS. In a further embodiment, remains chilling bag 20 may consist of a modified military approved Kappler Contaminated Remains Pouch (CRP). The CRP is constructed of ZYTRON® which is a barrier material that has shown barrier protection against Toxic Industrial Chemicals (TIC'S) and Chemical Warfare Agents (CWA's). The CRP is constructed using heat-sealed seams (inside and out), and incorporates a gas-tight zipper 48, a uni-directional pressure relief valve (not pictured) may be includes, as well as a fluid collection reservoir. The pressure relief valve would preferably be fitted to a C2AI NBC canister by way of an ISO-threaded coupling. This type of construction provides a hermetically-sealed remains pouch to protect against biological and chemical contamination for those dealing with the remains.

In a further embodiment, remains chilling bag 20 may include a temperature sensor and display (not pictured) operatively associated with the interior of remains chilling bag 20 for monitoring the core temperature of the bag for adequate cooling of the remains therein.

While a preferred embodiment of the invention has been described using specific terms, such description is for illustrative purposes only, and it is to be understood that changes and variations may be made without departing from the spirit or scope of the following claims.

What is claimed is:

1. A scalable and portable human remains cold storage system comprising:
   a chiller unit having a chilled fluid supply;
   a human remains chilling bag;
   a primary fluid supply line for supplying a chilled fluid for cooling human remains housed in the human remains chilling bag;
   a primary fluid return line for circulating warmed fluid back to the chiller unit for re-chilling the warmed fluid;
   a flow divider manifold;
   a plurality of secondary fluid supply lines, wherein each of the plurality of secondary fluid supply lines is removably connected to the flow divider manifold and is in fluid communication with the primary fluid supply line through the flow divider manifold and is in fluid communication with the human remains chilling bag;

a plurality of secondary return lines, wherein each of the plurality of secondary return lines is removably connected to the flow divider manifold and is in fluid communication with the primary fluid return line through the flow divider manifold and is in fluid communication with the human remains chilling bag;

wherein the flow divider manifold comprises a chamber, a chilled fluid input port configured to receive the primary fluid supply line, a warmed fluid return port configured to receive the primary fluid return line, a plurality of chilled fluid output ports configured to allow removable connection of the plurality of secondary fluid supply lines, and a plurality of warmed fluid input ports configured to allow removable connection of the plurality of secondary return lines; and whereby the scalable and portable human remains cold storage system is configured to allow chilled fluid to circulate through the human remains chilling bag and to allow warmed fluid that has circulated through the human remains chilling bag to return to the chiller unit for re-chilling in a continuous cycle through the flow divider manifold to maintain a desired temperature within the human remains chilling bag.

2. The scalable and portable human remains cold storage system of claim 1 further comprising a plurality of the flow divider manifolds in fluid communication with the primary fluid supply line.

3. The scalable and portable human remains cold storage system of claim 2 wherein the chilled fluid input port of each of the plurality of flow divider manifolds is configured to allow removable connection of the primary fluid supply line and the warmed fluid input port of each of the plurality of flow divider manifolds is configured to allow removable connection of the primary fluid return line.

4. The scalable and portable human remains cold storage system of claim 3 comprising quick connect couplings for each of the ports that are configured for removable connectivity.

5. The storage system of claim 1 wherein one of said chilled fluid output ports on a first flow divider manifold is connected in fluid communication with said chilled fluid input on a second flow divider manifold in a consecutive arrangement to that said chilled fluid from said primary fluid supply line passes through said first flow divider manifold before being received in said second flow divider manifold.

6. The storage system of claim 1 wherein the chiller unit is configured to supply the chilled fluid at a temperature of 30° F. to 45° F.

7. The scalable and portable human remains cold storage system of claim 1 wherein the chilled fluid includes approximately 30% by volume of glycol to prevent freezing.

8. The storage system of claim 1 wherein said chiller unit includes an outlet pressure reducing valve in fluid communication with said primary fluid supply line for providing a low flow pressure of said chilled fluid through the system.

9. The storage system of claim 8 wherein said low flow pressure of said chilled fluid through said primary fluid supply line is approximately 10 psi.

10. The storage system of claim 8 wherein said primary fluid line and said primary fluid return line are a 1" diameter for maintaining flow volume and pressure to said flow divider manifold.

11. The storage system of claim 10 wherein said secondary supply and return lines are ⅜" diameter for maintaining pressure and flow volume to circulate said fluid through said remains chilling bag.

12. The scalable and portable human remains cold storage system of claim 1 comprising quick connect couplings for each of the ports that are configured for removable connectivity.

13. The storage system of claim 1 wherein said remains chilling bag includes a top outer protective layer and a bottom outer protective layer releasably interconnected forming an interior cavity for storing remains.

14. The storage system of claim 13 including a first cooling pad carried by said top outer protective layer and a second cooling pad carried by said bottom outer protective layer wherein said first and second cooling pads are each connected in fluid communication with said secondary supply line and said secondary return line for circulating said chilled fluid through said remains chilling bad so that said remains placed in said interior cavity are cooled simultaneously from both a top and bottom side and returning warmed fluid to said chiller.

15. The storage system if claim 14 wherein said first and second cooling pads each include a flow director segmenting an interior fluid cavity in said cooling pads generally into a feed section and a return section so that said chilled fluid is circulated through said feed section into said return section un a consecutive one-way flow arrangement.

16. The storage system of claim 15 wherein said interior fluid cavity of said first and second cooling pads includes a plurality of fluid dispersion cells for directing said chilled fluid throughout said feed section and said return section.

17. The storage system of claim 14 wherein said first and second cooling pads are releasably carried by said top and bottom outer protective layers respectively for removal from said remains chilling bag.

18. The storage system of claim 14 including a first charcoal filter layer disposed between said top outer protective layer and said first cooling pad, and a second charcoal filter layer disposed between said bottom outer protective layer and second cooling pad for absorbing odors emitted from remains placed in said interior cavity.

19. The scalable and portable human remains cold storage system of claim 1 wherein the chilled fluid input port of the flow divider manifold is configured to allow removable connection of the primary fluid supply line and the warmed fluid input port is configured to allow removable connection of the primary fluid return line.

20. The scalable and portable human remains cold storage system of claim 19 comprising quick connect couplings for each of the ports that are configured for removable connectivity.

* * * * *